(12) United States Patent
Kim (10) Patent No.: US 11,179,504 B2
(45) Date of Patent: Nov. 23, 2021

(54) ENDOSCOPIC TREATMENT INSTRUMENT HAVING AN INNER AND OUTER TUBE

(71) Applicant: Changbo Kim, Gyeonggi-do (KR)

(72) Inventor: Changbo Kim, Gyeonggi-do (KR)

( * ) Notice: Subject to any disclaimer, the term of this patent is extended or adjusted under 35 U.S.C. 154(b) by 489 days.

(21) Appl. No.: 16/157,508

(22) Filed: Oct. 11, 2018

(65) Prior Publication Data

US 2019/0201591 A1  Jul. 4, 2019

(30) Foreign Application Priority Data

Dec. 29, 2017 (KR) .................. 10-2017-0183920

(51) Int. Cl.
| | |
|---|---|
| *A61L 31/14* | (2006.01) |
| *A61B 17/34* | (2006.01) |
| *A61B 1/018* | (2006.01) |
| *A61L 31/04* | (2006.01) |
| *A61M 25/00* | (2006.01) |

(52) U.S. Cl.
CPC ........ *A61L 31/041* (2013.01); *A61B 17/3478* (2013.01); *A61B 17/3496* (2013.01); *A61L 31/14* (2013.01); *A61B 1/018* (2013.01); *A61L 2400/10* (2013.01); *A61M 2025/0089* (2013.01)

(58) Field of Classification Search
CPC .... A61L 31/041; A61L 31/14; A61L 2400/10; A61L 29/049; A61L 29/041; A61L 29/04; A61L 2400/20; A61B 17/3496; A61B 17/3478; A61B 1/018; A61M 2025/0089; C08L 23/12; C08L 83/04; C08L 27/18
See application file for complete search history.

(56) References Cited

U.S. PATENT DOCUMENTS

| | | | | |
|---|---|---|---|---|
| 2004/0071988 A1* | 4/2004 | Nawrocki | .......... | A61B 17/3211 428/450 |
| 2005/0226993 A1* | 10/2005 | Nawrocki | ............... | A61L 31/10 427/2.1 |
| 2008/0208127 A1* | 8/2008 | Kuriyama | .......... | A61B 17/3478 604/164.01 |
| 2015/0225557 A1 | 8/2015 | Habimana et al. | | |

(Continued)

FOREIGN PATENT DOCUMENTS

| | | | | |
|---|---|---|---|---|
| JP | H0557018 A | 3/1993 | | |
| JP | 2001058006 | 3/2001 | ............... | A61B 1/00 |
| JP | 2001342359 A | 12/2001 | | |

(Continued)

OTHER PUBLICATIONS

Supplementary European Search Report, European Patent Office (EPO), Application No. EP 18896579, dated Mar. 15, 2021.

*Primary Examiner* — John P Leubecker
(74) *Attorney, Agent, or Firm* — Torchman IP LLC; Jonathan Torchman (57) ABSTRACT

An endoscopic treatment instrument including a dual tube inserted into a channel of an endoscope, the dual tube including an outer tube and an inner tube being inserted into the outer tube and moving forward and backward relative to the outer tube. The outer tube and the inner tube are made of a plastic material composed of a mixture of an organic polymer and a silicone compound, the organic polymer is polypropylene and the silicone compound is polydimethylsiloxane, and the polypropylene is 90 to 99.5 wt % and the polydimethylsiloxane is 0.5 to 10 wt %.

2 Claims, 5 Drawing Sheets

(56) References Cited

U.S. PATENT DOCUMENTS

2018/0117221 A1* 5/2018 Yatabe ................. C09D 183/06
2020/0343829 A1* 10/2020 Song ........................ H02N 1/04

FOREIGN PATENT DOCUMENTS

| JP | 2006230777 | | 9/2006 | ............... A61B 1/00 |
| JP | 2006271571 A | * | 10/2006 | |
| JP | 2006271571 A | | 10/2006 | |
| JP | 2012139463 | | 7/2012 | ............. A61B 18/14 |
| JP | 2013172842 A | | 9/2013 | |
| JP | 2015116242 A | | 6/2015 | |
| JP | 2016150229 | | 8/2016 | ............. A61B 18/12 |
| KR | 10-1287769 | | 7/2013 | ............... A61B 1/00 |
| WO | 2007046444 A1 | | 4/2007 | |
| WO | WO-2017002599 A1 | * | 1/2017 | ............. A61L 31/10 |

\* cited by examiner

ENDOSCOPIC TREATMENT INSTRUMENT HAVING AN INNER AND OUTER TUBE

This application relates to Korean Application No. 10-2017-0183920, filed Dec. 29, 2017, which is incorporated by reference in its entirety.

BACKGROUND OF THE INVENTION

Field of the Invention

The present invention generally relates to an endoscopic treatment instrument. More particularly, the present invention relates to an endoscopic treatment instrument, wherein a dual tube is provided which enables efficient manipulation and inexpensive manufacturing thereof.

Description of the Related Art

Generally, an endoscopic treatment instrument is introduced through the channel of an endoscope to a body cavity so as to perform various treatments for affected areas in the body cavity. In Japanese patent application publication No. 2001-58006, as an example of an endoscopic treatment instrument, an injection needle is disclosed which injects medicine fluid into an affected area in the body cavity.

The injection needle for endoscopy is provided with a thin and long insertion part inserted into a channel of an endoscope, the insertion part including a manipulation part provided on a base end part thereof. The insertion part is composed of a dual tube including an outer tube and an inner tube inserted into the outer tube so as to move forward/backward therein. The manipulation part performs the manipulation of moving the inner tube forward/backward relative to the outer tube. The inner tube includes a needle body of a through-hole shape provided on a front end part thereof. During the use of the injection needle for endoscopy, the insertion part of the injection needle for endoscopy is introduced through the channel of an endoscope into the body cavity. After that, the manipulation of the manipulation part allows the inner tube to move forward/backward relative to the outer tube. Accordingly, the needle body on the front end part of the inner tube protrudes to an outside of the outer tube from a front end part of the outer tube.

When an insertion part of the endoscope is inserted into a human body, the insertion part of the endoscope is bent in various forms according to shapes of tubes in the body cavity. When the insertion part of the injection needle for endoscopy is inserted through the channel of the endoscope into the body cavity, the insertion part of the injection needle for endoscopy is also bent in various forms according to the shape of the insertion part of the endoscope. Accordingly, in the case of treatment performed while the insertion part of the injection needle for an endoscopy is bent, when the inner tube moves forward/backward relative to the outer tube via the manipulation of the manipulation part, the frictional resistance between an outer circumferential surface of the inner tube and an inner circumferential surface of the outer tube increases. Accordingly, the dual tube constituting the insertion part of the injection needle for endoscopy requires high sliding mobility between the outer circumferential surface of the inner tube and the inner circumferential surface of the outer tube. Particularly, when the bending radius of the insertion part is small, the frictional resistance increases considerably. Consequently, the manipulability of the injection needle for an endoscopy decreases, and thus treating diseases safely is difficult and treatment time may increase.

Accordingly, the dual tube of the endoscopic treatment instrument is required to be hard to an appropriate degree, to not break when the bending radius is small, and to have a front end part efficiently controllable for precise treatment. In addition, the dual tube is required to have high workability, such as extrudability, for low manufacturing costs.

To meet such demands of the dual tube, various materials are used for the inner tube and the outer tube. The materials of the inner tube conventionally used include polytetrafluoroethylene (PTFE), ABS copolymer, polyethylene, nylon, and polypropylene, etc. PTFE is generally known as Teflon, which is the brand name of DuPont, and is famous for being chemically resistant to all chemicals and having a smooth surface. However, since PTFE has a high melting point of 320° C. to 346° C., it requires much heat in extruding, which causes high production cost. Further, FTFE has considerably low adhesiveness, which is an important factor in manufacturing a tube, and is high in material price. ABS copolymer is composed of acrylonitrile (A), butadiene (B), and styrene (S) and has high adhesiveness, and thus is widely used in injection products. However, as for ABS copolymer, it is difficult to form a thin tube in extruding, and when the tube is broken, efflorescence is produced. Polyethylene (PE) has a low melting point of 100° C. to 120° C., and is widely used due to excellent ductility and workability, but has low adhesiveness. Nylon has excellent material hardness, adhesiveness, and ductility. However, nylon has high flowability at a melting point, which causes difficulty in extruding a tube, and has high moisture absorption which changes the length thereof, and is thus unsuitable for an endoscopic treatment instrument in an environment having moisture. Since polypropylene (PP) has efficient workability, a low melting point of about 140° C., and is low in price, it is widely used.

PTFE, PP, and polycarbonate (PC) are used as the materials of the outer tube. Though PC has high adhesiveness and transparency and is used in products requiring high transparency, cleaning of PC metal molds is difficult after products are produced. Further, PC has a high melting point of 250° C. to 260° C.

DOCUMENTS OF RELATED ART (Patent Document 1) Japanese Patent Application Publication No. 2001-58006
(Patent Document 2) Korean Patent No. 10-1287769

SUMMARY OF THE INVENTION

Accordingly, the present invention has been made keeping in mind the above problems occurring in the related art, and the present invention is intended to propose an endoscopic treatment instrument, wherein the manipulation of the instrument is easy even when the bending radius thereof is small.

In addition, the present invention is intended to propose an endoscopic treatment instrument, wherein a safe treatment is possible in a short time.

Furthermore, the present invention is intended to propose an endoscopic treatment instrument, which does not break even when the bending radius of the instrument is small.

Additionally, the present invention is intended to propose an endoscopic treatment instrument, wherein the control of a front end part is easy so as to facilitate precise treatment.

Furthermore, the present invention is intended to propose an endoscopic treatment instrument having low manufacturing cost due to high workability.

In order to achieve the above object, according to one aspect of the present invention, there is provided an endoscopic treatment instrument, including: a dual tube inserted into a channel of an endoscope, the dual tube including an outer tube and an inner tube being inserted into the outer tube and moving forward and backward relative to the outer tube, wherein since the outer tube of the dual tube is made of a plastic material having a silicone compound added to an organic polymer, when the inner tube moves forward and backward along the channel relative to the outer tube while the dual tube is bent, frictional resistance between an outer circumferential surface, which is a sliding movable surface of the inner tube, and an inner circumferential surface, which is a sliding movable surface of the outer tube, is lower than frictional resistance therebetween when the outer tube and the inner tube of the dual tube are all made of an organic polymer alone.

Preferably, the inner tube of the dual tube may be made of a plastic material having a silicone compound added to an organic polymer.

Preferably, since the inner tube includes protruding parts provided on an outer circumferential surface thereof, frictional resistance between the outer circumferential surface of the inner tube and the inner circumferential surface of the outer tube may be lower than frictional resistance therebetween when the inner tube does not include the protruding parts provided on the outer circumferential surface thereof.

Preferably, the organic polymer may be polypropylene and the silicone compound may be polydimethylsiloxane. In addition, the polypropylene may be 90 to 99.5 wt % and the polydimethylsiloxane may be 0.5 to 10 wt %.

The endoscopic treatment instrument of the present invention mentioned above has little frictional resistance between the outer circumferential surface of the inner tube and the inner circumferential surface of the outer tube of the dual tube, so that even when the bending radius thereof is small, the endoscopic treatment instrument facilitates easy manipulation and safe treatment in a short time. In addition, according to the present invention, the endoscopic treatment instrument allows the dual tube to have a low frictional resistance and to be made of hard materials, so that even in the state of a low bending radius, the endoscopic treatment instrument is not easily broken, distal end thereof is easy to control, and precise treatment is facilitated. Furthermore, according to the endoscopic treatment instrument of the present invention, the dual tube can be made of materials that are inexpensive and have low frictional resistances, and are processed with excellent workability when they are subjected to an extrusion molding process and to an adhesion process using a bonding agent, thereby leading to a very low manufacturing cost of the endoscopic treatment instrument.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinbelow, exemplary embodiments of the present invention will be described in detail with reference to the accompanying drawings.

Figure 1:
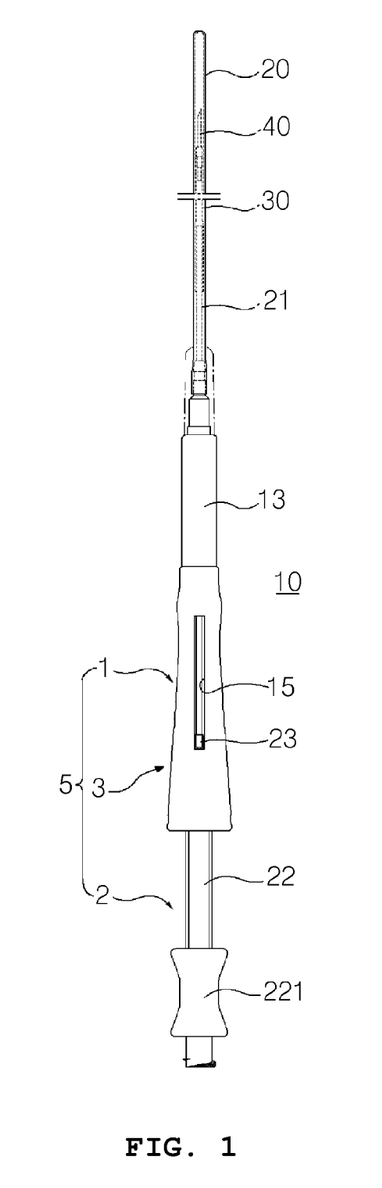
FIG. 1 is a view showing an endoscopic treatment instrument according to a first embodiment of the present invention.
Figure 2:
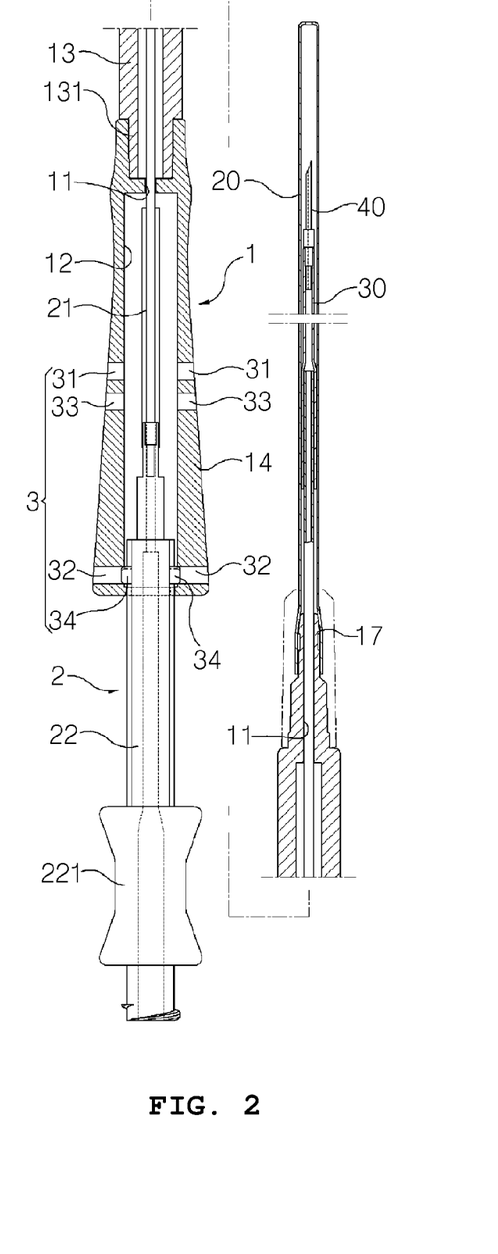
FIG. 2 is a cross-sectional view of the endoscopic treatment instrument shown in FIG. 1.
Figure 3A:
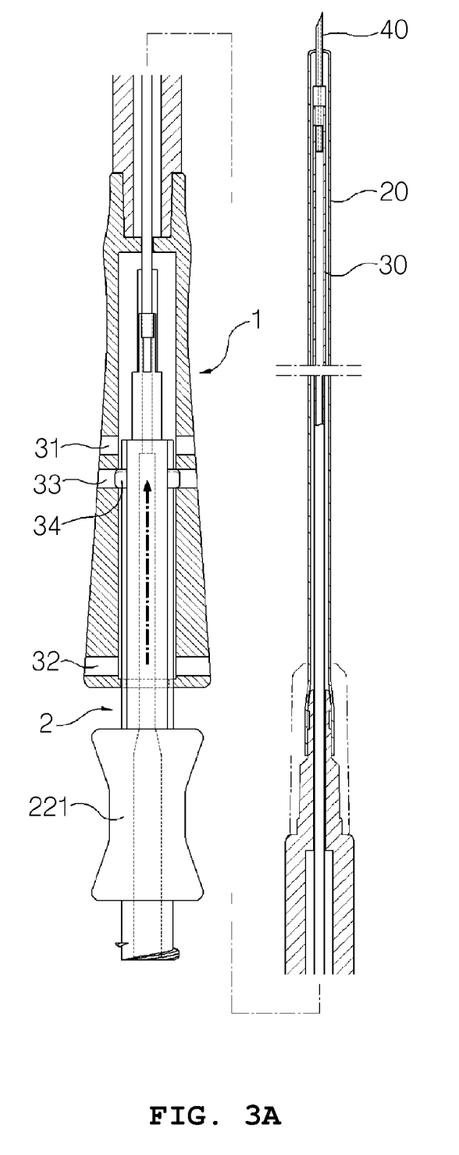
FIG. 3A and FIG. 3B are views showing states of a needle protruding from the endoscopic treatment instrument shown in FIG. 1.
Figure 3B:
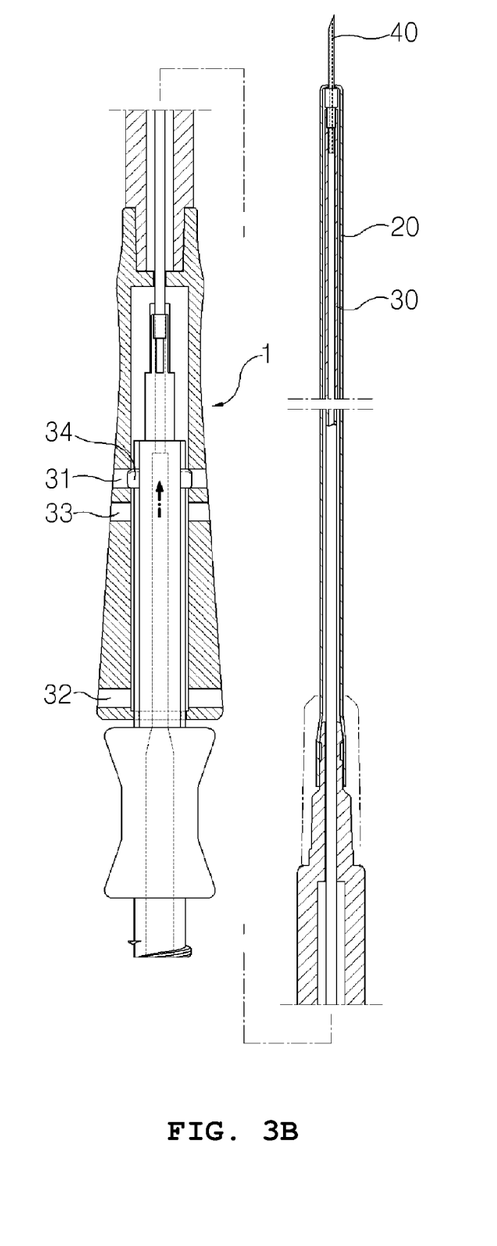

FIG. 1 is a view showing an endoscopic treatment instrument 10 according to a first embodiment of the present invention, and FIG. 2 is a cross-sectional view of the endoscopic treatment instrument 10 shown in FIG. 1. FIG. 3A and FIG. 3B are views showing states of a needle protruding from the endoscopic treatment instrument 10 shown in FIG. 1.

An inner tube 30 is imbedded in an outer tube 20, and causes a through hole needle 40 to protrude from a front end part of the outer tube 20. The through hole needle 40 is mounted to the front end part of the inner tube 30 so as to communicate with the outer tube, and the manipulation part 5 is connected to a rear end part of the inner tube 30. The manipulation part 5 moves the inner tube 30 forward or backward relative to the outer tube 20 such that the through hole needle 40 protrudes from the front end part of the outer tube 20.

The manipulation part 5 includes a body tube 1, an operation member 2 inserted into the body tube 1 so as to move forward and backward therein, and a position adjustment part 3 provided between the body tube 1 and the operation member 2, the position adjustment part adjusting a position of the through hole needle 40 in three levels, for example, by holding a movement position of the operation member 2 at a third level.

The body tube 1 includes a needle through hole 11 provided on a front of an inner part thereof and an operation hole 12 provided on a rear of an inner part thereof, the operation hole 12 being extended more in diameter than the needle through hole 11. The body tube 1 includes a shaft tube part 17 provided on a front thereof, wherein a rear end part of the outer tube 20 is inserted into and fixed to the shaft tube part 17.

In addition, the body tube 1 is configured to be divided into a front body tube 13 and a rear body tube 14 for efficient repair in case of malfunction in the body tube. The front body tube 13 includes an insertion connection tube 131 provided on a rear thereof, the insertion connection tube 131 being inserted into a front of the rear body tube 14 such that the front body tube 13 and the rear body tube 14 are divided.

The operation member 2 is inserted into the body tube 1 so as to move forward/backward therein such that the through hole needle 40 protrudes from the front end part of the outer tube 20. The operation member 2 includes an operation through hole needle 21 provided on a front thereof, wherein a front end part of the operation through hole needle is connected to the inner tube 30, and a manipulation through hole tube 22 provided on a rear thereof, wherein the manipulation through hole tube is inserted into the operation hole 12.

The rear body tube 14 includes position holding holes 15 provided on opposite sides thereof, and the manipulation through hole tube 22 of the operation member 2 includes position holding protrusions 23 provided on opposite sides of a front thereof, wherein the position holding protrusions move forward and backward while being inserted into the position holding holes 15. The position holding holes 15 and the position holding protrusions 23 prevent the operation member 2 from running idle or deviating from the body tube 1 during the use of the manipulation part 5.

The manipulation through hole tube 22 has an injection fluid supply tube (not shown) connected to a rear end thereof, and includes a janggu-shaped handle part 221 provided on a rear thereof for easy holding by doctors.

The position adjustment part 3 is provided between the body tube 1 and the operation member 2, the position adjustment part adjusting a position of the through hole needle 40 in three levels, for example, by holding a movement position of the operation member 2 in a third level. The position adjustment part 3 includes three pairs of perpendicular holes 31, 32, 33 provided perpendicularly to the operation hole 12 of the body tube 1.

Holding protrusions 34 are provided by protruding from front parts of the manipulation through hole tube 22, and as the operation member 2 moves forward or backward, the holding protrusions are held in one pair of the three pairs of perpendicular holes 31, 32, 33. Additionally, the holding protrusions 34 are provided by protruding from the manipulation through hole tube 22 so as to have a hemispheric shape such that the manipulation part 5 is efficiently manipulated forward or backward.

Accordingly, the endoscopic treatment instrument 10 includes the perpendicular holes 33 provided between the perpendicular holes 31 and the perpendicular holes 32 of the body tube 1, so that a protruded length of the through hole needle 40 may be manipulated in two levels. When the manipulation part 5 is used to protrude the through hole needle 40 from the front end part of the outer tube 20, the protruded length of the through hole needle 40 may be manipulated in two levels according to a doctor's treatment type or disposition. Here, since the protruded length of the through hole needle 40 can be changed, the length of the needle and needle-piercing strength can be adjusted. More specifically, when protruding the entire length of the through hole needle 40, the manipulation through hole tube 22, which was moved backward, moves forward to the maximum and the holding protrusions 34 provided on the manipulation through hole tube 22 are held in the perpendicular holes 31, and accordingly, the entire length of the through hole needle 40 is protruded and is pierced in a human body. In this case, the exposed length of the protruded through hole needle 40 reaches maximum, and since the inner tube 30 moves forward with maximum stroke in the outer tube 20, the needle-piercing strength also reaches maximum.

When piercing the needle in a human body without protruding the entire length of the through hole needle 40, the manipulation through hole tube 22, which was moved backward, moves forward, and the holding protrusions 34 are held in the perpendicular holes 33 positioned right behind the perpendicular holes 31, thus the entire length of the through hole needle 40 is not protruded.

Since the endoscopic treatment instrument 10 is used to treat affected areas in a human body, the outer tube 20 and the inner tube 30 are required to have appropriate hardness and appropriate manipulability. The manipulability is determined by the material quality and the thicknesses of the outer tube 20 and the inner tube 30, and the interval therebetween.

In embodiments of the present invention, the outer tube 20 and the inner tube 30 of endoscopic treatment instrument 10 are made of the same material that can achieve manufacturing convenience. When the outer tube 20 and the inner tube 30 are made of the same material, affinity generally increases, and the frictional resistance between sliding movable surfaces increases. Accordingly, in the embodiments of the present invention, the outer tube 20 and the inner tube 30 are made of the same organic polymer and silicone compound having high slipperiness is added thereto so as to decrease frictional resistance between the outer tube 20 and the inner tube 30.

In consideration of workability, material price, and hardness, polypropylene (PP) is preferred as the organic polymer. Polydimethylsiloxane (PDMS) is preferred as the silicone compound.

The PP may be 90 to 99.5 wt %, and the silicone compound may be 0.5 to 10 wt %. Excessive ductility occurring due to the addition of 10 wt % or more the silicone compound to the PP is not suitable for an endoscopic treatment instrument, and when 0.5 wt % less the silicone compound is added to the PP, the characteristics of silicon are not manifested, which causes low slipperiness.

The PP is hard, and since though the inner tube and the outer tube are all configured according to the size of an endoscope, a front end part thereof is easy to control and a bending elastic modulus is large, thus the tubes are not easily broken even in a small bending radius.

Figure 4:
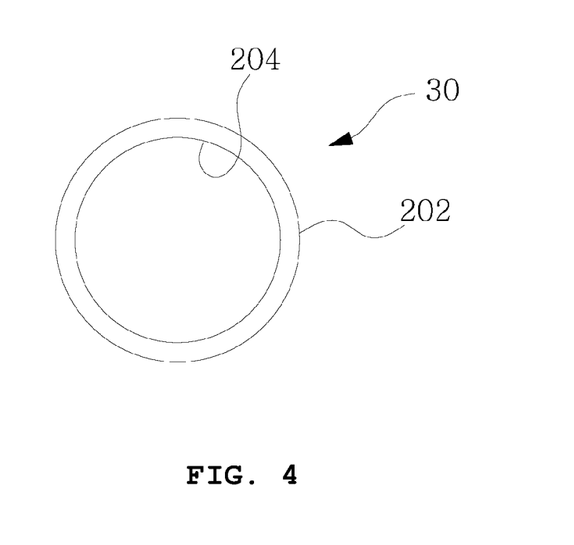
FIG. 4 is a cross-sectional view of an inner tube of the endoscopic treatment instrument shown in FIG. 1.

FIG. 4 is a cross-sectional view of the inner tube 30 of the endoscopic treatment instrument shown in FIG. 1. As shown in FIG. 4, an outer circumferential surface 202 and an inner circumferential surface 204 of the inner tube 30 are even. Since the outer circumferential surface 202 of the inner tube 30 is in contact with the inner circumferential surface 204 of the outer tube 20 in a large area, frictional resistance between the inner tube 30 and the outer tube 20 is relatively large.

Figure 5:
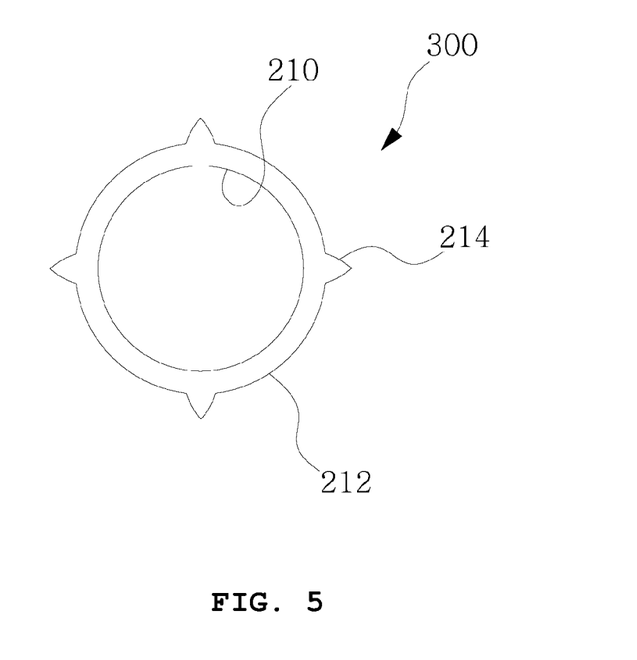
FIG. 5 is a cross-sectional view of an inner tube of an endoscopic treatment instrument according to a second embodiment of the present invention.

FIG. 5 is a cross-sectional view of an inner tube 300 of an endoscopic treatment instrument according to a second embodiment of the present invention. As shown in FIG. 5, though an inner circumferential surface 210 of the inner tube 300 is configured to have an even surface so as not to prevent the flow of medicine fluid, an outer circumferential surface 212 is configured to have protruding parts 214 so as to decrease an area in contact with an outer tube.

Table 1 shows manipulabilities when the material of the outer tube is polytetrafluoroethylene (PTFE). The inner tube 30 is inserted into the outer tube 20, the outer tube 20 is wound on a cylinder 160 mm in diameter, the inner tube 30 is connected to a push pull gauge, and the inner tube 30 is pulled. In this case, a pulled strength of the inner tube 30 is measured when the inner tube 30 comes out of the outer tube 20. In view of a maximum length of each instrument used in gastroscopy and colonoscopy, length of the outer tube 20 is set to be 2500 mm. All cross-sections of the outer tube 20 are circular.

Manipulabilities are tested when there is moisture on a contact surface of the outer tube 20 with the inner tube 30 and when there is no moisture thereon. The manipulabilities are tested when the inner tube 30 does not move in the outer tube 20 any longer and is broken. Since the test stops when the inner tube 30 does not move in the outer tube 20 at a given strength and is about to be broken, the manipulability values (manipulation forces, N) in an experiment shown in table 1 may be larger than measured manipulability values.

TABLE 1

| | Outer tube | | | | Inner tube | | | | Manipulability (N) | |
|---|---|---|---|---|---|---|---|---|---|---|
| NO | Material quality | Outer diameter mm | Inner diameter mm | Thickness mm | Material quality | Tube cross-section | Outer diameter mm | Inner diameter mm | Thickness mm | Moisture X | Moisture ○ |
| 1 | PTFE | 2.4 | 1.7 | 0.35 | PTFE | Circle | 1.4 | 1.0 | 0.2 | 4 | 6 |
| 2 | PTFE | 2.4 | 1.7 | 0.35 | ABS | Circle | 1.4 | 0.6 | 0.4 | 3 | 5 |
| 3 | PTFE | 2.4 | 1.7 | 0.35 | PE | Circle | 1.5 | 1.0 | 0.25 | 10 | 11↑ |
| 4 | PTFE | 2.4 | 1.7 | 0.35 | Nylon6 | Circle | 1.3 | 0.9 | 0.2 | 3 | 6 |
| 5 | PTFE | 2.4 | 1.7 | 0.35 | PP | Circle | 1.4 | 1.0 | 0.2 | 3 | 3 |
| 6 | PTFE | 2.4 | 1.7 | 0.35 | PP | Protrusion | 1.4 | 1.0 | 0.2 | 2 | 1 |
| 7 | PTFE | 2.4 | 1.7 | 0.35 | PP + silicon | Circle | 1.5 | 1.0 | 0.25 | 6 | 12 |
| 8 | PTFE | 2.4 | 1.7 | 0.35 | PP + silicon | Protrusion | 1.5 | 1.0 | 0.25 | 1 | 3 |

Table 2 shows manipulabilities when the material of the outer tube is the polycarbonate (PC).

TABLE 2

| | Outer tube | | | | Inner tube | | | | Manipulability (N) | |
|---|---|---|---|---|---|---|---|---|---|---|
| NO | Material quality | Outer diameter mm | Inner diameter mm | Thickness mm | Material quality | Tube cross-section | Outer diameter mm | Inner diameter mm | Thickness mm | Moisture X | Moisture ○ |
| 9 | PC | 2.4 | 1.8 | 0.3 | PTFE | Circle | 1.4 | 1.0 | 0.2 | 3 | 6 |
| 10 | PC | 2.4 | 1.8 | 0.3 | ABS | Circle | 1.4 | 0.6 | 0.4 | 5 | 30↑ |
| 11 | PC | 2.4 | 1.8 | 0.3 | PE | Circle | 1.5 | 1.0 | 0.25 | 6 | 10↑ |
| 12 | PC | 2.4 | 1.8 | 0.3 | Nylon6 | Circle | 1.3 | 0.9 | 0.2 | 6 | 16↑ |
| 13 | PC | 2.4 | 1.8 | 0.3 | PP | Circle | 1.4 | 1.0 | 0.2 | 8 | 17↑ |
| 14 | PC | 2.4 | 1.8 | 0.3 | PP + silicon | Circle | 1.5 | 1.0 | 0.25 | 8 | 17↑ |
| 15 | PC | 2.4 | 1.8 | 0.3 | PP + silicon | Protrusion | 1.5 | 1.0 | 0.25 | 4 | 15 |

Table shows manipulabilities when the material of the outer tube is the polypropylene (PP).

TABLE 3

| | Outer tube | | | | Inner tube | | | | Manipulability (N) | |
|---|---|---|---|---|---|---|---|---|---|---|
| NO | Material quality | Outer diameter mm | Inner diameter mm | Thickness mm | Material quality | Tube cross-section | Outer diameter mm | Inner diameter mm | Thickness mm | Moisture X | Moisture ○ |
| 16 | PP | 2.4 | 1.8 | 0.3 | PTFE | Circle | 1.4 | 1.0 | 0.2 | 1 | 2 |
| 17 | PP | 2.4 | 1.8 | 0.3 | ABS | Circle | 1.4 | 0.6 | 0.4 | 2 | 16↑ |
| 18 | PP | 2.4 | 1.8 | 0.3 | PE | Circle | 1.5 | 1.0 | 0.25 | 13↑ | 13↑ |
| 19 | PP | 2.4 | 1.8 | 0.3 | Nylon6 | Circle | 1.3 | 0.9 | 0.2 | 3 | 20↑ |
| 20 | PP | 2.4 | 1.8 | 0.3 | PP | Circle | 1.4 | 1.0 | 0.2 | 17 | 20↑ |
| 21 | PP | 2.4 | 1.8 | 0.3 | PP + silicon | Circle | 1.5 | 1.0 | 0.25 | 5 | 20↑ |
| 22 | PP | 2.4 | 1.8 | 0.3 | PP + silicon | Protrusion | 1.5 | 1.0 | 0.25 | 20↑ | 7 |

Table 4 shows manipulabilities when the material of the outer tube is the compound of polypropylene (PP) and the silicone compound.

TABLE 4

| | Outer tube | | | | Inner tube | | | | Manipulability (N) | |
|---|---|---|---|---|---|---|---|---|---|---|
| NO | Material quality | Outer diameter mm | Inner diameter mm | Thickness mm | Material quality | Tube cross-section | Outer diameter mm | Inner diameter mm | Thickness mm | Moisture X | Moisture ○ |
| 23 | PP + silicon | 2.4 | 1.8 | 0.3 | PTFE | Circle | 1.4 | 1.0 | 0.2 | 0 | 0 |
| 24 | PP + silicon | 2.4 | 1.8 | 0.3 | ABS | Circle | 1.4 | 0.6 | 0.4 | 0 | 10 |

TABLE 4-continued

| | Outer tube | | | | Inner tube | | | | Manipulability (N) | |
|---|---|---|---|---|---|---|---|---|---|---|
| NO | Material quality | Outer diameter mm | Inner diameter mm | Thickness mm | Material quality | Tube cross-section | Outer diameter mm | Inner diameter mm | Thickness mm | Moisture X | Moisture ○ |
| 25 | PP + silicon | 2.4 | 1.8 | 0.3 | PE | Circle | 1.5 | 1.0 | 0.25 | 1 | 9↑ |
| 26 | PP + silicon | 2.4 | 1.8 | 0.3 | Nylon6 | Circle | 1.3 | 0.9 | 0.2 | 2 | 14↑ |
| 27 | PP + silicon | 2.4 | 1.8 | 0.3 | PP | Circle | 1.4 | 1.0 | 0.2 | 2 | 10 |
| 28 | PP + silicon | 2.4 | 1.8 | 0.3 | PP + silicon | Circle | 1.5 | 1.0 | 0.25 | 1 | 11 |
| 29 | PP + silicon | 2.4 | 1.8 | 0.3 | PP + silicon | Protrusion | 1.5 | 1.0 | 0.25 | 0 | 2 |

Nylon 6 is not suitable for the endoscopic treatment instrument due to length change caused by moisture absorption. According to the embodiments of the present invention, the material of the outer tube 20 and the inner tube 30 is the compound of the PP and the silicone compound, and when the protruding parts 214 are provided on the outer circumferential surface of the inner tube 30, the manipulation force is measured to be 2N when there is moisture, and to be zero N when there is no moisture. That is, though there is moisture as in a human body, 2N or less external forces are required when the inner tube 30 slides passing through the outer tube 20.

Distance of the outer circumferential surface of the inner tube 30 and the inner circumferential surface of the outer tube 20 being spaced apart from each other is preferably 0.2 to 0.5 mm. Another factor influencing the manipulability is the thicknesses of the outer tube 20 and the inner tube 30. To obtain excellent manipulability, the thickness of the outer tube 20 is preferably 0.3 to 0.35 mm, and the thickness of the inner tube 30 is preferably 0.2 to 0.4 mm.

Although the embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An endoscopic treatment instrument, comprising:
a dual tube inserted into a channel of an endoscope, the dual tube including an outer tube and an inner tube being inserted into the outer tube and moving forward and backward relative to the outer tube,
wherein the outer tube and the inner tube are made of a plastic material composed of a mixture of an organic polymer and a silicone compound, the organic polymer is polypropylene and the silicone compound is polydimethylsiloxane, and the polypropylene is 90 to 99.5 wt % and the polydimethylsiloxane is 0.5 to 10 wt %.

2. The endoscopic treatment instrument of claim 1, wherein the inner tube includes protruding parts provided on an outer circumferential surface thereof.

* * * * *